United States Patent [19]
Schmitt

[11] Patent Number: 5,879,947
[45] Date of Patent: Mar. 9, 1999

[54] APPARATUS AND METHOD FOR DETECTING DMAH USING PARTICLE SENSING DETECTOR

[75] Inventor: John V. Schmitt, Sunnyvale, Calif.

[73] Assignee: Applied Materials, Inc., Santa Clara, Calif.

[21] Appl. No.: 870,871

[22] Filed: Jun. 6, 1997

[51] Int. Cl.⁶ .......................... G01N 21/47; G01N 21/53
[52] U.S. Cl. ............................... 436/73; 422/83; 422/91; 250/381; 250/574; 356/438
[58] Field of Search ............... 252/305, 9; 250/380–382, 250/573–574; 356/432, 436–439; 422/83, 88, 91; 436/73, 164, 178

[56] References Cited

PUBLICATIONS

Merton Bunker, Jr., "Working Knowledge—Smoke Detectors," Scientific American, Apr. 1997, p. 116.

*Primary Examiner*—Lyle A. Alexander
*Attorney, Agent, or Firm*—Patterson & Associates

[57] ABSTRACT

A method for detecting dimethylaluminumhydride (DMAH) comprises sensing the aluminum oxide particles produced by the reaction of the DMAH with air (or with a small amount of oxygen). This is accomplished using a particle-sensing device, such as those commonly used to detect smoke, particularly an ionization-type detector.

12 Claims, 5 Drawing Sheets

APPARATUS AND METHOD FOR DETECTING DMAH USING PARTICLE SENSING DETECTOR

BACKGROUND OF THE INVENTION

1. Field of the Invention

This invention relates to the detection of dimethylaluminumhydride (DMAH) and equipment useful for such detection. More particularly, the invention relates to an apparatus and method for detecting DMAH using a particle detecting apparatus, specifically, and ionization-type detector.

2. Background of the Related Art

The processing of semiconductor wafers often requires the formation of thin films of material. These thin films are often formed utilizing Chemical Vapor Deposition (CVD) techniques that sometimes require the use of materials that are in their liquid phase at room temperature. One such material is DMAH which serves as a source for aluminum in the production of thin films.

To introduce DMAH into a CVD reaction vessel, the liquid material is charged in a bubbler. A carrier gas is introduced through a nozzle immersed within the liquid in the bubbler at a rate controlled by a mass-flow controller. This generates bubbles of the carrier gas within the DMAH liquid which ascend through the liquid. As a result, the DMAH is vaporized into and becomes mixed with the carrier gas. The carrier gas containing the DMAH vapor is then introduced into the reaction vessel for subsequent deposition onto the substrate to form a thin film. Accordingly, any leaks in the vessel and related delivery lines will allow the DMAH vapor to escape. As DMAH is pyrophoric, any leak must be immediately detected. However, without adequate detection apparatus, DMAH cannot be used for the commercial production of film layers because of the fire risk it presents. Known techniques for detecting DMAH include gas chromatography, which examines a sample of the gas for its constituents, and provides a "signature" of the gas. This signature is then compared, typically manually, to a known DMAH signature, to determine the presence of DMAH. This detection method is expensive, time consuming, and somewhat operator dependant. Where leakage of a pyrophoric gas such as DMAH is to be detected, this method is unacceptable in a manufacturing environment, because unacceptable quantities of gas would leak before detection of the leak occurs. This need for detection of gas leakage is equally applicable to other gases, particularly other pyrophoric gases used in manufacturing processes.

Presently though, there are no known devices to detect gaseous DMAH which has escaped from the DMAH delivery system.

SUMMARY OF THE INVENTION

In view of the foregoing, it is an object of the invention to provide an apparatus and method for detecting DMAH, and other gases which may be conveniently and readily reacted with an ambient environment to form a measurable reaction product. It is another object of the invention to provide a safety warning of the presence of DMAH or other gases in the atmosphere or in a controlled environment, i.e., that which has escaped from the delivery system, at a relatively low cost. Yet another object is to utilize existing, reliable technology to provide a detection system that is both reliable and easy to implement and manufacture. Other objects of the invention will become apparent from time to time throughout the specification and claims as hereinafter related.

In accordance with the invention, a method for detecting DMAH includes detecting the DMAH using a particle-detecting apparatus. In the preferred embodiment, the particle-detecting apparatus is a ionization-type detector that is believed to detect the $Al_2O_3$ particles produced as a result of the exposure of DMAH to an oxygen containing environment, such as ambient air.

In one embodiment of the invention, the invention is a system for detecting DMAH in an enclosure. The enclosure includes a bubbler for vaporizing the DMAH and an exhaust port for venting the enclosure. An ionization detector is positioned in the enclosure, preferably in the exhaust port of the enclosure, to detect the presence of particulate residue of the DMAH with air. The detector includes a signal to warn of a DMAH leak. The invention is equally applicable to the detection particulate residues from other reactant materials and thus, may also be used to detect gases other than DMAH.

BRIEF DESCRIPTION OF THE DRAWINGS

These and other objects and advantages of the invention will be apparent when read in conjunction with the accompanying drawings wherein.

DETAILED DESCRIPTION OF THE PREFERRED EMBODIMENT

The present invention contemplates the detection of gaseous or liquid compounds, including leaks thereof, by the detection of particulate products produced by reaction of the gaseous material within the ambient environment. In one commercial embodiment, it is useful for detecting leakage of DMAH, thus enabling commercial use of this pyrophoric agent. Dimethylaluminumhydride (DMAH) is a compound used to produce thin films in the processing of semiconductor wafers. When exposed to an environment containing oxygen, the DMAH reacts with the oxygen to form very small $Al_2O_3$ (Aluminum Oxide) particles. The present invention uses a particle-detecting apparatus 10 to warn of the presence (or non-presence) of DMAH by detecting the presence of $Al_2O_3$.

A preferred embodiment will be described below with reference to the use of a particle detecting apparatus 10 used to detect DMAH in gas box on a process system having a DMAH bubbler system. However, the invention is not limited to this apparatus for the particle-detecting apparatus 10 may be positioned anywhere there is a potential for DMAH leakage or spillage or where DMAH is used.

Additionally, the present invention may be used to detect particles produced as a result of other gaseous reactions. In particular, the present invention may be used in other applications where detection of a gas is desired. For example, other metal precursors react with the atmosphere or other gaseous environments to produce metal oxide particles. Often, these gases are pyrophoric and, thus, require detection or detection is otherwise needed. The present invention may be used to detect these other gases by detecting the produced particles in the same way that it detects DMAH leakage by the presence of $Al_2O_3$ particles. However, far clarity and ease of description, the following description primarily focuses on the detection of DMAH although the present invention is equally applicable to the other gases.

Likewise, the following description describes the reaction of DMAH with oxygen or the atmosphere which contains oxygen. The present invention is equally applicable to any other reactions wherein the gas to be detected reacts with some other gas to produce particles. For example, the present invention may be charged with nitrogen or any other reactive gas that reacts with the gas to be detected and through the reaction forms particles. Accordingly, the present invention is not limited to the use of oxygen or atmosphere as the reactive gas.

Figure 1:
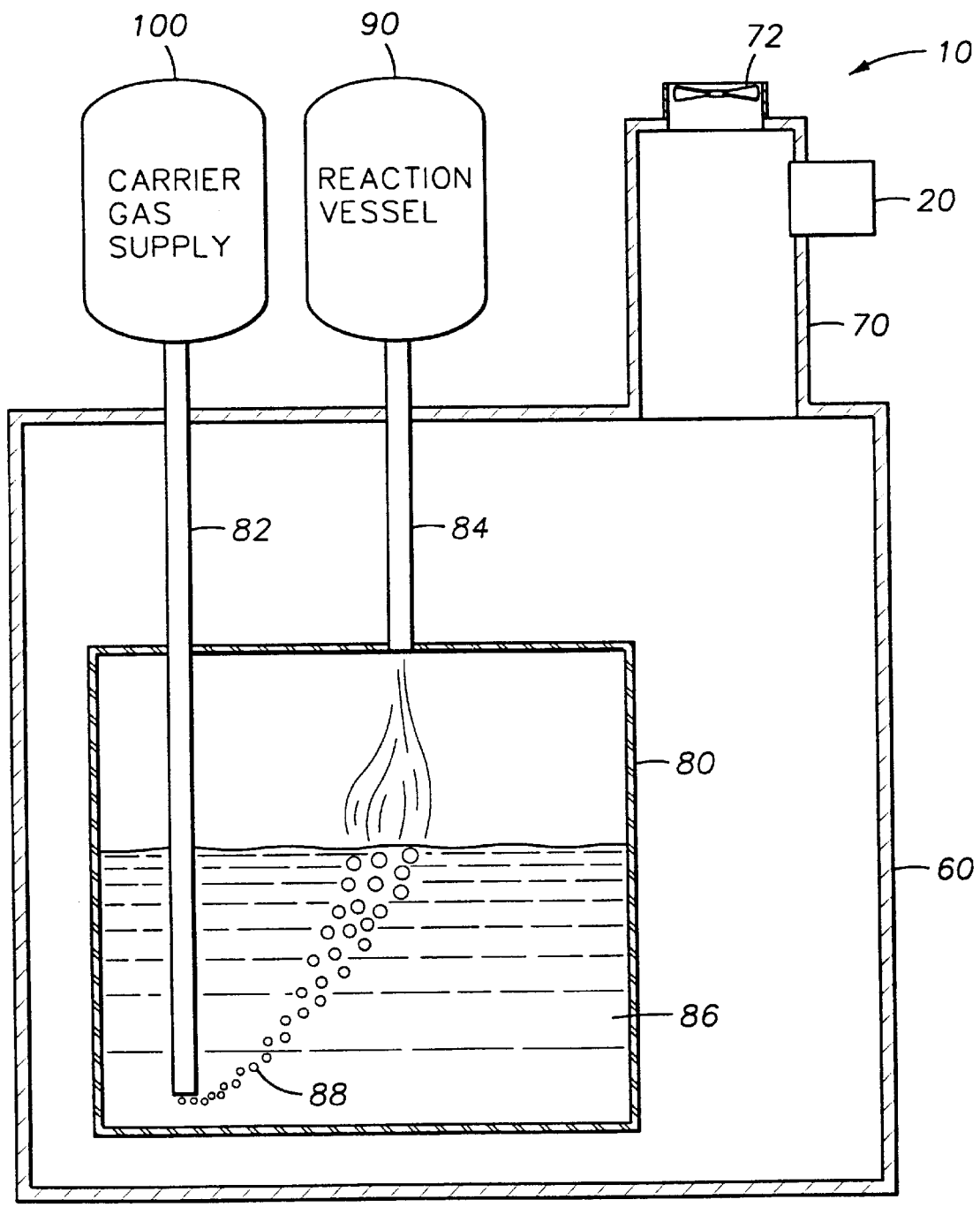
FIG. 1 is a schematic view of the bubbler enclosure having a particle-detecting apparatus positioned in the exhaust port.
Figure 2:
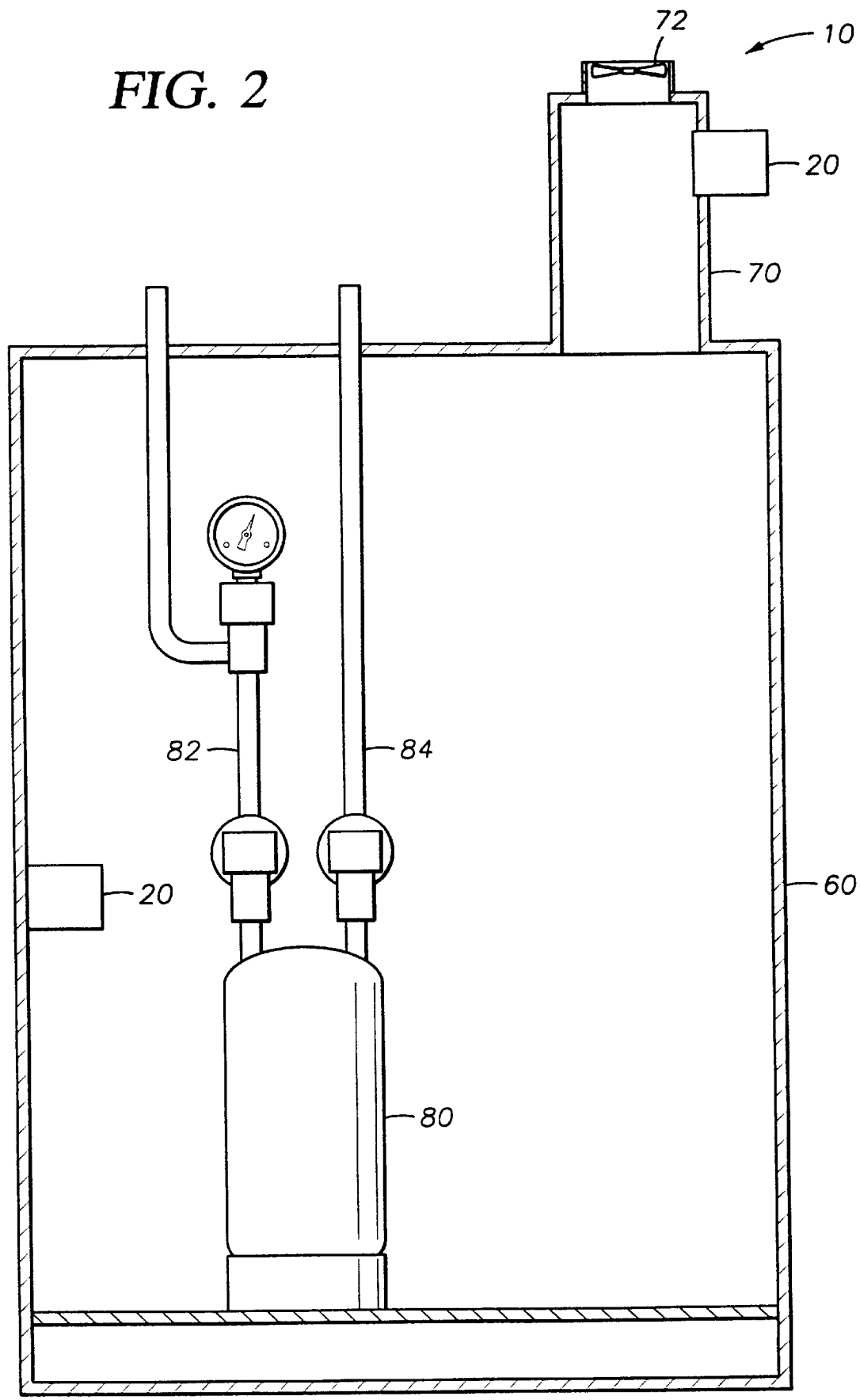
FIG. 2 is a front cross sectional view of the bubbler enclosure having a particle-detecting apparatus positioned in the exhaust port.

Thin films of aluminum are produced using a Chemical Vapor Deposition (CVD) process wherein a vapor state of the DMAH decomposes at the surface to be coated thereon. FIGS. 1 and 2 show a typical bubbler system used to convert the liquid DMAH 86 into the required vapor. The vaporization process is typically carried out in an enclosure 60. A bubbler 80 positioned within the enclosure 60 includes an inlet pipe 82 and an outlet pipe 84. The inlet pipe 82 extends into the bubbler 80 and terminates at a position proximal the bottom of the bubbler 80. The lower terminus of the inlet pipe 82 is open and may include a nozzle and is maintained below the level of the DMAH liquid 86.

A carrier gas supply 100 in fluid communication with the inlet pipe 82 supplies the carrier gas to the bubbler 80 through the inlet pipe 82. As the carrier gas exits the inlet pipe 82 at a controlled rate, it forms bubbles 88 within the DMAH liquid 86 that rise toward the surface. As the bubbles 88 rise, the DMAH is vaporized into and becomes mixed with the carrier gas. The carrier gas rises above the surface of the DMAH liquid and enters the open end of the outlet pipe 84 which is positioned at the top of the bubbler 80. The outlet pipe 84 provides fluid communication from the bubbler 80 to the reaction vessel 90 where the DMAH is deposited on the desired surface.

Often, the enclosure 60 includes an exhaust port 70 that has a fan 72 disposed therein. The exhaust port 72 facilitates the venting of the enclosure 60 and is typically connected to an approved venting or waste disposal system.

In the prior art, DMAH leaking from the gas delivery system piping, fittings, bubbler, etc. could be detected by gas chromatography, or by the visual presence of fire in the gas box. However, both detection schemes are unsatisfactory for commercial manufacturing environments. Applicant has discovered that when a leak occurs, the airborne DMAH vapor is believed to react with the air, or even small levels of oxygen, one byproduct of which is $Al_2O_3$ (aluminum oxide) which precipitates out as very small particles, and which may be ionized and detected in the same manner that standard combustion products are detected by smoke detectors (e.g., that is by using a particle-detecting apparatus 10). As a result, applicant has discovered a means of easily, rapidly detecting a DMAH leak before a fire or other unacceptable consequence of the leak occurs.

Figure 3:
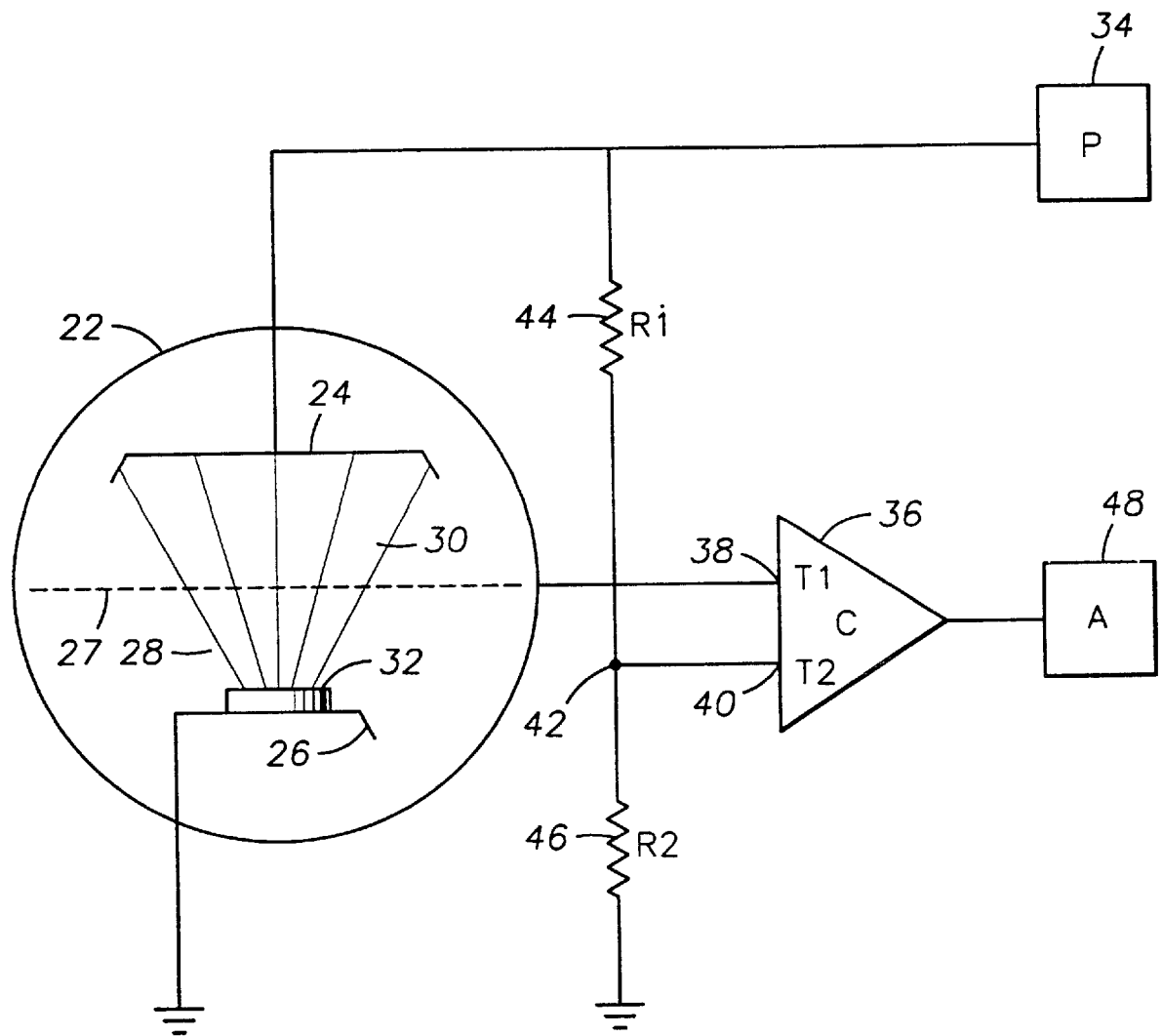
FIG. 3 is a schematic view of a ionization-type detector.

A common type of particle detector is an ionization-type detector 20. Since their commercial introduction in 1969, they have become a common type of smoke detector installed in homes. A schematic diagram of a common ionization-type detector 20 is shown in FIG. 3. The ionization-type detector 20 has a housing encasing an inner electrode 26, an outer electrode 24, and a collector electrode 27. The housing may be filled simply with atmospheric air or may be charged with same other reactive gas. The electrodes are spaced to define both an inner chamber 28 between the inner electrode 26 and the collector electrode 27, and an outer chamber 30 between the collector electrode 27 and the outer electrode 24.

An ionization source 32 within the housing 22 ionizes the air molecules, for example, with alpha particles from a radioactive material, such as americium 241, which provides an ion current flow when connected to a power source 34. The outer electrode 24 and inner electrode 26 are connected across the power source 34. This produces an ion current flow of a definite magnitude that flows between the inner electrode 26 and the outer electrode 24 when clean air, or another known reactive gas mixture of gases, is in the ionization-type detector 20.

This ion current flow establishes a voltage on the collector electrode 27 of a predetermined value which is applied to the first terminal 38 of a comparator 36. This voltage to the first terminal 38 is compared to a reference voltage established at the second terminal 40 of the comparator 36. The reference voltage is established from the junction 42 of a voltage divider consisting of a first resistor 44 and a second resistor 46 connected in series across the power source 34.

When aluminum oxide particles enter the chamber, they attach to the ions and reduce the ion current flow which reduces the voltage on the collector plate. As an example, in one ionization type detector 20 having a power supply voltage of 9 volts, the voltage on the collector electrode 27 is 5.5 volts during clean air conditions. The resistor values produce a reference voltage at the second terminal 46 of 4.5 volts. When the aluminum oxide particle density within the chamber is sufficient to reduce the collector electrode voltage to 4.5 volts, the comparator 36 produces an output to the alarm actuating device 48. Although this example discloses a common ionization-type detector 20, the exact design may be constructed, and tuned, to detect small variations in the voltage resulting from small amounts of particles within the detector 20 as desired. Ionizing of the detector 20 involves determining the appropriate voltage on the collector electrode 27 when aluminum oxide particles are present in the detector, so that the $Al_2O_3$ particles are readily detected, and adjusting or providing a resistance to produce a reference voltage at the second terminal 46 equal to this appropriate desired voltage.

Figure 4:
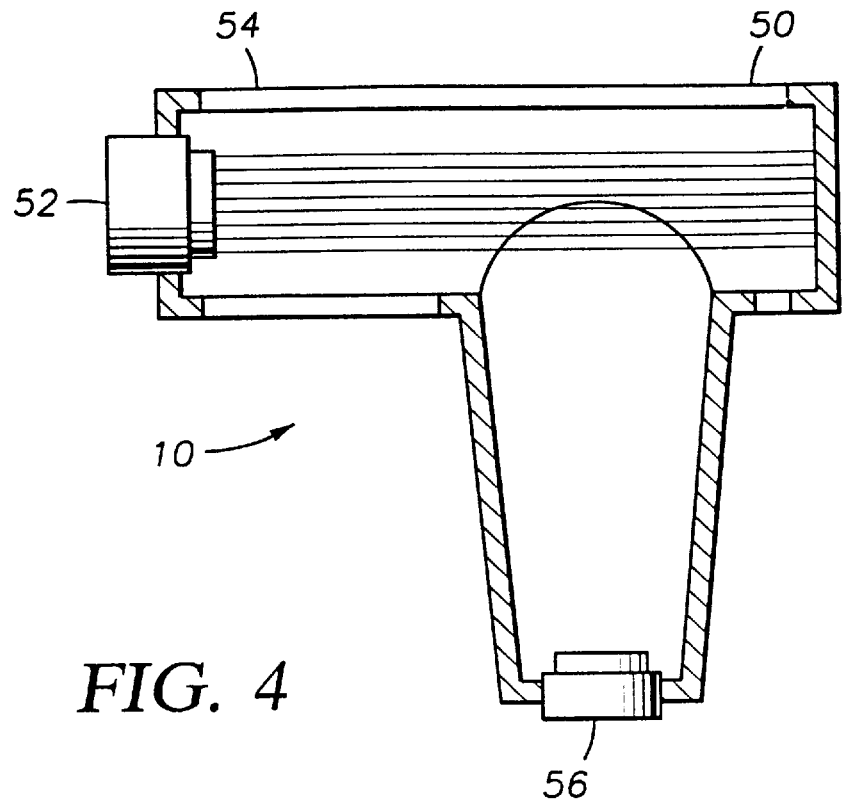
FIG. 4 is a side cross sectional view of a photoelectric detector during clean air conditions.
Figure 4A:
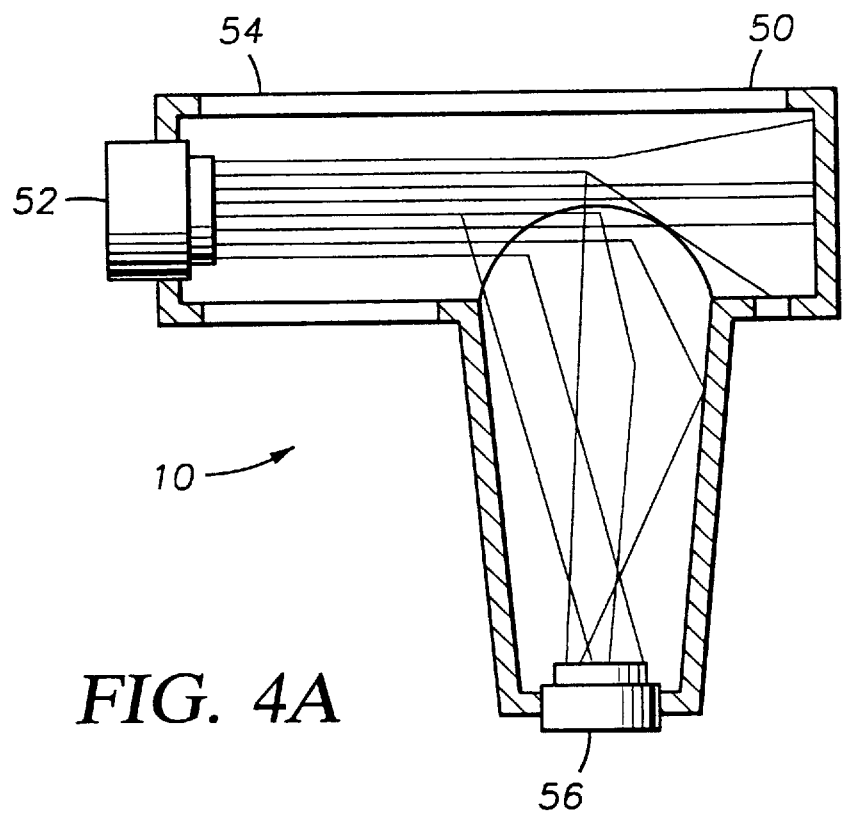
FIG. 4a is a side cross sectional view of a photoelectric detector with aluminum oxide particles therein.

The above description of ionization-type detectors 20 describes a common design for such detectors 20. Variations from the basic design do not affect the applicability of the ionization-type detectors 20 to the sensing of aluminum oxide particles produced as a byproduct of the reaction of DMAH with air or small amounts of oxygen. Further, other types of particle-sensing apparatuses 10 may be used to detect the aluminum oxide without departing from the scope of the invention. Additionally, as previously described, the ionization-type detector 20 may be used to detect particles produced by the reaction of other gases with oxygen, the atmosphere, or other reactive gases (e.g., the ionization-type detector 20 may be used to detect the presence of other metal oxide particles produced from a reaction of another metal precursor with the atmosphere) without departing from the scope of the invention. An example of another type of detector is a common photoelectric detector 50 (FIGS. 4 and 4a) that functions by employing a light emitting diode 52 that sends beams of light unimpeded across a chamber 54.

When particles enter the chamber 54, the light scatters. A photocell 56 positioned at an angle to the diode 52 senses the scattered light and sets off an alarm.

Any type of alarm indicator, whether audible, visual or both, may be connected to the particle-detecting apparatus 10 to warn of DMAH leakage in the environment. Likewise, any known control system may be connected to the particle-detecting apparatus 10 to perform a desired task in the event of a leak. For example, when the particle-detecting apparatus 10 detects a leak, the control system may actuate a visual and audible warning, send a signal to an operator station indicating the location of the warning, and shut down the process until the leak is repaired.

Accordingly, the method for detecting DMAH comprises sensing the aluminum oxide particles produced from the reaction of DMAH and oxygen. This is accomplished using a particle detecting apparatus 10 which is preferably an ionization-type detector 20. Likewise, a method for detecting other types of gases comprises sensing the particles produced from a reaction of the gas with a reactive gas.

As applied to the bubbler system, the particle-detecting apparatus 10 is preferably positioned proximal the exhaust port 70 although it may also be positioned at other locations within the enclosure 60, such as near the bubbler 80. By positioning the particle-detecting apparatus 10 within the enclosure 60, the particle-detecting apparatus 10 is positioned where the leaks are most likely to occur and where the highest concentrations of DMAH, or other gas to be detected, from a leak are present. Therefore, this positioning enhances the likelihood of detecting a leak of DMAH or other gas to be detected. Note that the enclosure 60 may be charged with a reactive gas, just as the housing of the ionization-type detector 20 may be charged. The reactive gas being selected to react with the gas to be detected to generate particles. Consequently, the particle detecting apparatus 10 may be used to detect gases that do not react with atmosphere to form particles, but react with other reactive gases to form particles that may be detected thereby.

Figure 5:
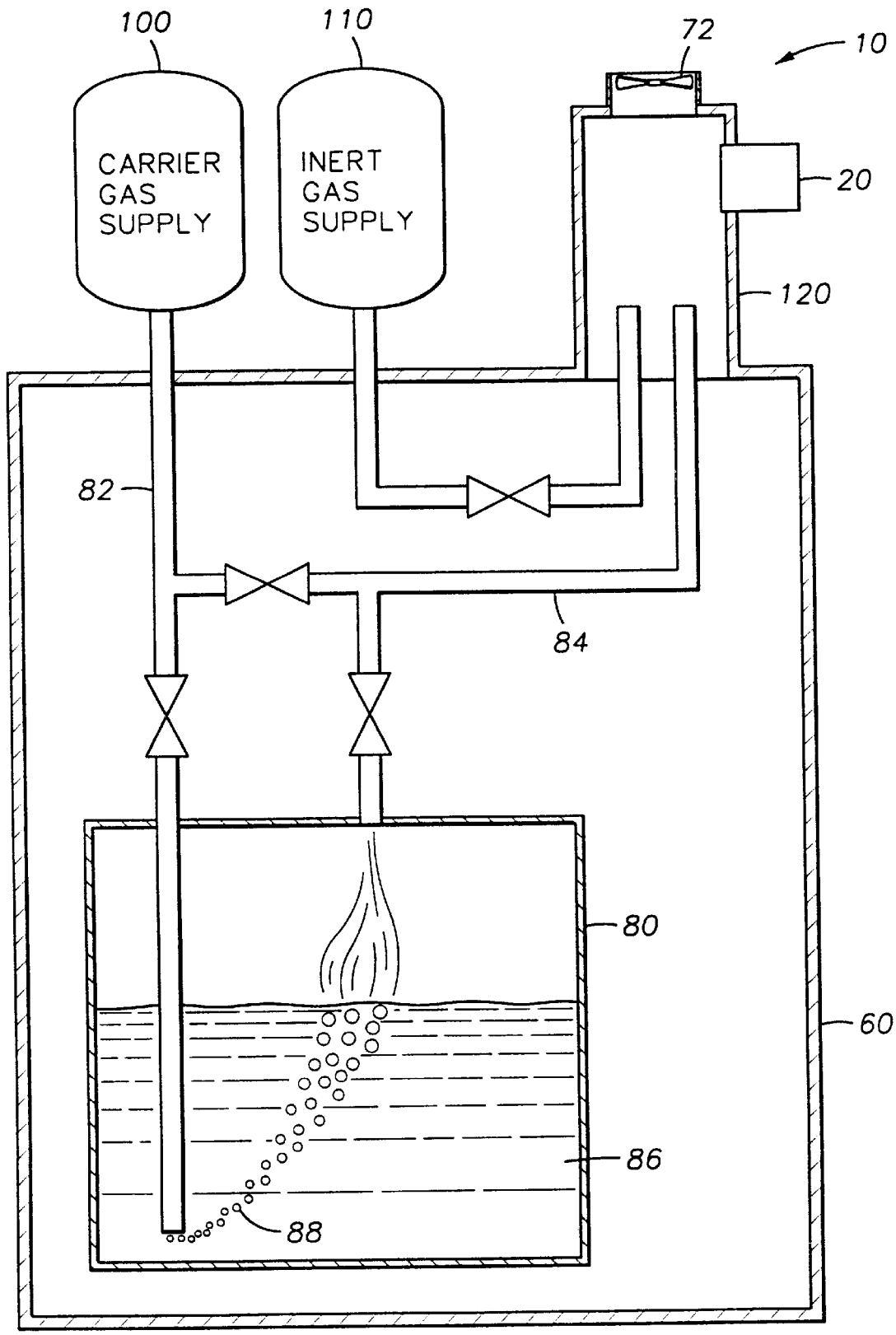
FIG. 5 is a schematic view of a test apparatus.

An ionization-type detector was tested to determine its effectiveness at sensing DMAH leaks. A schematic of the test apparatus is shown in FIG. 5. The test apparatus includes a carrier gas supply 100 in fluid communication, through an inlet pipe 82 with a bubbler 80. The inlet pipe 82 extends proximal the bottom of the bubbler 80 so that the carrier gas is released below the surface of the DMAH liquid 86. The released carrier gas forms bubbles 88 in the DMAH liquid 86 that ascend to the surface. During their ascent, the DMAH is vaporized into the bubbles 88. The carrier gas containing the DMAH then exits the bubbler 80 through an outlet pipe 84.

However, the test apparatus directs the vaporized DMAH and carrier gas through the outlet pipe 84 to the bottom of a test chamber 120. A fan 72 at the open top of the test chamber 120 controls the airflow in the test chamber 120. An inert gas supply 110 in fluid communication with the bottom of the test chamber 120 facilitates displacement of the oxygen in the test chamber 120. The ionization-type detector 20 is mounted in the test chamber 120. For the purposes of the test, the ionization-type detector 20 used was originally manufactured by Applied Materials, Inc. of Santa Clara, Calif. as part number 1400-01047.

The sensitivity of the ionization-type detector 20 was then tested under two conditions. In one condition, the "atmospheric" condition, the fan was turned on to create airflow in the test chamber and to simulate an air exhaust on an enclosure 60. In the second condition, the "semi-inert" condition, the fan was turned off, the bottom was sealed, and the inert gas from the inert gas supply 110 was allowed to flow into the test chamber 120. Accordingly, in the semi-inert condition, most of the oxygen is displaced from the test chamber 120.

The ionization-type detector 20 was then tested at various carrier gas flow rates and temperatures. In the test, the maximum flow rate of the DMAH gas was about 1.5 sccm and the maximum molar percentage of DMAH was about 0.3 to 0.4 percent. The results of the test, shown in the following table, indicate whether the ionization-type detector 20 sensed the DMAH in the test chamber 120.

| Carrier Gas Flow Rate | Condition | Temperature | DMAH Detected? |
| --- | --- | --- | --- |
| 100 sccm | atmospheric | 30° C. | No |
| 150 sccm | atmospheric | 30° C. | No |
| 200 sccm | atmospheric | 30° C. | Yes |
| 250 sccm | atmospheric | 30° C. | Yes |
| 500 sccm | atmospheric | 30° C. | Yes |
| 500 sccm | atmospheric | 45° C. | Yes |
| 500 sccm | semi-inert | 45° C. | Yes |

As shown by the test results, the ionization-type detector 20 is effective at sensing the presence of DMAH in the atmosphere or even in conditions wherein only a small amount of oxygen is present. Based upon these results, it is apparent that an ionization-type detector 20 will effectively detect the presence of DMAH.

I claim:

1. A method for detecting dimethylaluminumhydride (DMAH), comprising:

providing a particle sensor;

providing a reactant material which, when contacted with DMAH, results in the formation of particulate matter; and detecting the particulate matter with the particulate sensor.

2. The method of claim 1 wherein said particle sensor is an ionization-type detector.

3. The method of claim 1 wherein said particle sensor is a photoelectric detector.

4. A method for detecting dimethylaluminumhydride (DMAH), comprising sensing the aluminum oxide particles produced as byproduct of the reaction of DMAH and oxygen.

5. The method of claim 4 further comprising sensing said aluminum oxide particles using a particle-detecting device.

6. The method of claim 4 further comprising sensing said aluminum oxide particles using an ionization-type detector.

7. The method of claim 4 wherein said particle-sensing detector is a photoelectric detector.

8. A dimethylaluminumhydride (DMAH) detection system, comprising:

an enclosure, a bubbler in the enclosure adapted to vaporize the DMAH with a carrier gas;

a material reactant with DMAH to form particulate matter as a reaction product with DMAH; and a particle-detecting device disposed in communication with the enclosure.

9. The system of claim 8 wherein the particle-detecting device is an ionization-type detector.

10. The system of claim 8 wherein the particle-detecting device is a photoelectric detector.

11. The system of claim 8 wherein the particle-detecting device is positioned proximal the bubbler.

12. The system of claim 8 wherein:

the enclosure has an exhaust port; and the particle-detecting device is positioned in the exhaust port.

* * * * *